United States Patent
Bodis-Wollner et al.

(10) Patent No.: US 9,230,045 B2
(45) Date of Patent: Jan. 5, 2016

(54) LAYER-BY-LAYER QUANTIFICATION OF THE REMODELING OF THE HUMAN FOVEA IN NEURODEGENERATIVE DISEASE

(75) Inventors: Ivan Bodis-Wollner, Brooklyn, NY (US); Ivan Selesnick, Brooklyn, NY (US)

(73) Assignees: The Research Foundation for The State University of New York, Albany, NY (US); New York University, New York, NY (US)

( * ) Notice: Subject to any disclaimer, the term of this patent is extended or adjusted under 35 U.S.C. 154(b) by 159 days.

(21) Appl. No.: 13/983,854

(22) PCT Filed: Feb. 15, 2012

(86) PCT No.: PCT/US2012/025229
§ 371 (c)(1),
(2), (4) Date: Jan. 16, 2014

(87) PCT Pub. No.: WO2012/112675
PCT Pub. Date: Aug. 23, 2012

(65) Prior Publication Data
US 2014/0122029 A1  May 1, 2014

Related U.S. Application Data

(60) Provisional application No. 61/443,002, filed on Feb. 15, 2011.

(51) Int. Cl.
*G06K 9/00* (2006.01)
*G06F 17/50* (2006.01)
(Continued)

(52) U.S. Cl.
CPC ............ *G06F 17/5009* (2013.01); *G06T 19/20* (2013.01); *A61B 3/102* (2013.01); *G06F 19/3437* (2013.01); *G06T 2210/41* (2013.01); *G06T 2219/2012* (2013.01)

(58) Field of Classification Search
None
See application file for complete search history.

(56) References Cited

U.S. PATENT DOCUMENTS 7,768,652 B2   8/2010  Everett
2003/0114740 A1*  6/2003  Essock et al. ................. 600/407
(Continued)

OTHER PUBLICATIONS

Mohammedyusuf E. Hajee, et al., Inner Retinal Layer Thinning in Parkinson Disease, Arch Ophthalmol, (Jun. 2009) vol. 127, No. 6, pp. 737-741.

(Continued)

*Primary Examiner* — Shervin Nakhjavan
(74) *Attorney, Agent, or Firm* — Scully, Scott, Murphy & Presser, P.C.

(57) ABSTRACT

A system and method for layer-by-layer quantification of the remodeling of the human fovea comprises finding a fixed reference point in inner retina, measuring the thickness of the inner retina at the fixed reference point, for a range of finely sampled distances starting from the fixed reference point, measuring the thickness, comparing the measured thickness with a normative base and obtaining a plurality of curves, evaluating area for each curve and defining a distance from the fixed reference having highest sensitivity with respect to the fixed reference point compared to the normative base, displaying a 3D re-creation of foveal architecture-based color-coded picture in accordance with the measured thickness at each finely sampled distance, entering the measured thickness into a model having parameters, obtaining numerical solutions for each parameter, and defining percent change of the parameters for the patient versus the parameters for the control.

9 Claims, 10 Drawing Sheets

(51) Int. Cl.
*G06T 19/20* (2011.01)
*A61B 3/10* (2006.01)
*G06F 19/00* (2011.01)

(56) References Cited

U.S. PATENT DOCUMENTS

2007/0287932 A1* 12/2007 Huang et al. .................. 600/558
2009/0033868 A1* 2/2009 Huang et al. .................. 351/205
2010/0220914 A1 9/2010 Iwase et al.
2011/0200531 A1* 8/2011 Tan ................................ 424/9.2
2011/0275931 A1* 11/2011 Debuc ........................... 600/425

OTHER PUBLICATIONS

International Search Report dated Jun. 19, 2012 issued in PCT/US2012/025229.

* cited by examiner

The Retinal Thickness of Healthy Individuals vs Those of PD Patients[a]

Table. The Retinal Thickness of Healthy Individuals vs Those of PD Patients[a]

| Retinal Area | Retinal Thickness, μm | | P Value |
|---|---|---|---|
| | Healthy Individuals | PD Patients | |
| Superior IRL | 103.5 (24.3) | 88.79 (11.3) | .01 |
| Inferior IRL | 104 (23.5) | 89.83 (11.1) | .01 |
| Superior ORL | 170.2 (23.8) | 170.4 (7.67) | .88 |
| Inferior ORL | 168.2 (22.9) | 167.9 (7.86) | .99 |

Abbreviations: IRL, inner retinal layer; ORL, outer retinal layer; PD, Parkinson disease.
[a] Data are presented as mean (SD).

FIGURE 9

LAYER-BY-LAYER QUANTIFICATION OF THE REMODELING OF THE HUMAN FOVEA IN NEURODEGENERATIVE DISEASE

CROSS REFERENCE TO RELATED APPLICATIONS

The present invention claims the benefit of U.S. provisional patent application 61/443,002 filed Feb. 15, 2011, the entire contents and disclosure of which are incorporated herein by reference as if fully set forth herein.

FIELD OF THE INVENTION

The present invention relates generally to diagnosis techniques for neurodegenerative diseases, and, more particularly, to using imaging techniques and optical tomography as diagnosis techniques.

BACKGROUND OF THE DISCLOSURE

Parkinson's Disease (PD) is worldwide the second most-common neurodegenerative disorder. Its diagnosis is based on clinically observable "cardinal" motor symptoms that are attributed to the loss of dopamine-producing nerve cells in one area of the brain. Dopamine is the critical neuropharmacological facilitator between nerve cells affected in PD. However, by the time cardinal motor symptoms appear, over 60% of the neurons are lost thus complicating interventional strategies as the disease process is rather advanced. Early markers or identification of at-risk patients would vastly improve therapeutic outcomes for neuroprotective types of therapy.

The eye is a window to the brain. Many processes which affect the brain also affect the back of the eye. Optical Coherence Tomography (OCT) is a commercially available diagnostic equipment that is widely used by ophthalmologists and optometrists. OCT is an optical signal acquisition and processing method that has been used in the study of ocular physiology and pathology since 1991. OCT allows imaging of the back of the eye and measuring with great precision changes in its nerve cells. The technique takes little time, typically five minutes, is non-invasive and the equipment is available in many doctors' offices. The test yields imaging and quantification of the thickness of the retina of the eye. The resolution of in-vivo retinal imaging using OCT is around five microns. This resolution is not sufficient to distinguish different cell types of the retina.

Over the last decades it has become apparent that non-motor systems, including vision, are affected by PD, with the retina being one site of pathology. PD apparently selectively affects certain retinal nerve layers and there is a remodeling of the retina in PD. The effects of PD in the human retina are consistent with results obtained in experimental models in monkeys and rodents. Impaired retinal processing in PD and in the monkey model of PD were originally shown by electroretinographic (ERG) recordings. The pattern ERG is determined by retinal ganglion cell activity and predominantly reflects foveal visual processing, which normally mediates optimum contrast and color vision. However, the ERG is not ideal to serve as a clinical large scale diagnostic tool.

The remodeling and pathology of PD can be quantified using OCT. For the differential diagnosis of PD and for potential follow-up of patients undergoing therapy with so-called neuroprotective drugs, the OCT may be a tool: non-invasive, widely available and relatively inexpensive. OCT has been used in neurology research to look at the thinning of the surface of the retina in Multiple Sclerosis and related demyelinating disorders. These layers can be seen on fundoscopy, a routine ophthalmological procedure. In recent years electroretinographic evidence of fovealdysfuncion of the retina in PD was supported by OCT. This can be used to form three-dimensional images from within any optical scattering medium. The currently used spectral-domain OCT (SD-CT) achieves micrometer-resolution and can be used to visualize different layers of the multilayered neural tissue of the retina. Thinning of the most superficial, inner layer, the so-called nerve fiber layer (NFL), was first reported in PD 2004. Several subsequent studies corroborated that the NFL is thinned in PD. These data raised some hopes that OCT may be useful as a biomarker for PD. However there are hurdles in the way of adopting OCT for multicenter large scale biomarker studies.

One problem is that there are differences in the quantification programs developed by the three major OCT equipment manufacturers. As a result, retinal thickness data are not simply transferable. The two most widely used equipments, RT-VUe and Zeiss Cirrus have different sampling rates and yield different thickness values for the same eye.

Another problem is that OCT, as almost every imaging technique, yields masses of data and it is unclear what measures and what thickness of the retina one should compare across equipments.

In addition, OCT thickness measurements are either based on the manufacturers' automated programs or manual measurements. Automated programs are geared to the diagnosis of glaucoma or maculopathy, neither of these programs are specifically suited to PD. Manual measurements not only require many repeats but also entail variability and vagaries due to reference line fitting and distortions introduced by the equipment's software for imaging.

Neurologists currently do not use OCT as a diagnostic tool for PD because there is no methodology to quantify the layers below the ganglion cells. Hence there is no technique to evaluate a patient for PD or other neurological disorders using data and/or information obtained from OCT.

SUMMARY OF THE INVENTION

An inventive system and method for layer-by-layer quantification of the remodeling of the human fovea is presented. The novel system for layer-by-layer quantification of the remodeling of the human fovea comprises a CPU, a display device, and a module operable to find a fixed reference point in the inner retina, measure the thickness at the fixed reference point, for a range of finely sampled distances starting from the fixed reference point, measure the thickness of the inner retina at each finely sampled distance, compare, at each finely sampled distance, the measured thickness with a normative base and obtain a plurality of curves for signal/noise ratios, evaluate area for each curve and obtain a set of areas defining a distance from the fixed reference having highest sensitivity with respect to the fixed reference point compared to the normative base, create and display, on the display device, a three dimensional re-creation of foveal architecture-based color-coded picture in accordance with the measured thickness at each finely sampled distance, enter the measured thickness into a model having parameters, obtain numerical solutions for each parameter for a patient and for a control of the model, and define percent change of the parameters for the patient versus the parameters for the control.

A method for layer-by-layer quantification of the remodeling of the human fovea comprises steps of finding a fixed reference point in the inner retina, measuring the thickness of the inner retina at the fixed reference point, for a range of finely sampled distances starting from the fixed reference point, measuring the thickness at each finely sampled distance, comparing, at each finely sampled distance, the measured thickness with a normative base and obtaining a plurality of curves for signal/noise ratios, evaluating area for each curve and obtaining a set of areas defining a distance from the fixed reference having highest sensitivity with respect to the fixed reference point compared to the normative base, creating and displaying a three dimensional re-creation of foveal architecture-based color-coded picture in accordance with the measured thickness at each finely sampled distance, entering the measured thickness into a model having parameters, obtaining numerical solutions for each parameter for a patient and for a control of the model, and defining percent change of the parameters for the patient versus the parameters for the control.

In one aspect, the model comprises a Gaussian function having three parameters and a polynomial function having four parameters. In one aspect, the Gaussian function is a zero-mean bivariate Gaussian function and the polynomial function is a second-order bivariate polynomial.

A computer readable storage medium storing a program of instructions executable by a machine to perform one or more methods described herein also may be provided.

BRIEF DESCRIPTION OF THE DRAWINGS

These and other features, aspects, and advantages of the apparatus of the present invention will become better understood with regard to the following description, appended claims, and accompanying drawings where:

FIG. 9 is a table of retinal thickness of healthy individuals and PD patients.

DETAILED DESCRIPTION OF DISCLOSURE

Figure 1:
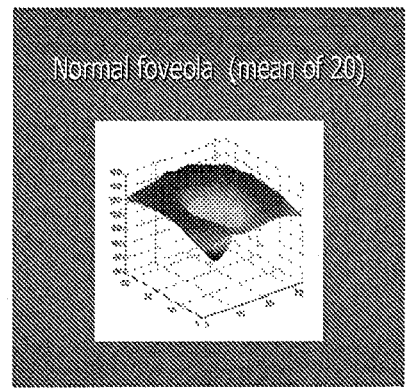
FIG. 1 illustrates a normal foveola.

The retina contains several layers at different depths and each layer is histologically different. The area of the retina devoted to most acute vision, known as the fovea, does not contain all retinal layers. The fovea looks like a crater. At the very center of the foveal retina, in the foveola or foveal pit, only photoreceptors are found. At the sides of the foveal crater, different retinal layers begin to emerge at different depths, that is, at different distances from the center of the crater.

Given that each of the different layers in the fovea contains different cell types, it is possible to refine the diagnosis of various disorders that affect the retina. One non-ophthalmological disorder or disease is Parkinson Disease (PD).

Retinal thickness can be sampled and quantified at various distances in 0.25 mm steps from the center of the foveal pit. In the normal retina, there is first the outer nuclear layer starting around 0.3 mm of the foveola and the inner nuclear layer starting around 0.8 mm. Experimental results show that the thinning of the retina in PD is most pronounced in the inner retina surrounding the central most point, the foveola.

Fourier-domain OCT can be used for the measuring and imaging of the inventive technique. One of the many advantages of the high speed of Fourier-domain OCT is that it can allow the transformation from two-dimensional to three-dimensional imaging. The overall image quality of Fourier-domain OCT is also superior because of the elimination of many motion artifacts from the increased speed of acquisition. This is particularly relevant in PD patients with tremor. The axial resolution of a time-domain OCT is 8 to 10 µm, whereas for Fourier-domain OCT it is approximately 5 µm, which results in a more accurate representation of retinal topography.

A novel algorithm to define depth of different layers in the fovea, using the OCT, is presented. The inventive technique separates retinal layers with their different cellular compositions, by finding a fixed reference point in the anatomy of the retina. This fixed point is the foveola, which is the center of a pit. The walls of the pit are sloping and at each distance from the center of the fovea one finds an increasing contribution of new cellular elements. The inventive technique then measures the thickness of the inner retina, or inner retina layer (IRL), over a range of finely sampled distances starting from the foveal pit. This establishes the retinal layer that contributes to the thickness at that location or distance from the starting point. Accordingly, in the case of a specific individual or particular subject, one can quantify which retinal layer and which set of cells are most affected.

At each distance, the measured result is compared with a normative base. The comparison uses a statistical/signal analytical tool known as receiver operator characteristics (ROC). ROC yields curves for signal/noise ratios. The normative base can be a "golden" standard, e.g., data developed on healthy subjects for the age group.

Next, each curve is evaluated for its area, e.g., Area Under the Curve (AUC). A set of AUCs define the distance from the foveal pit where the highest sensitivity discriminates the subject's retina from healthy controls. From a set of AUCs, the one with the largest area can be identified. This distance can then define the emergence of a given retinal layer. With ROC and AUC, one establishes the specificity and sensitivity, e.g., confidence limits, for the classification of any subject's retina as "normal" or "abnormal". The results are amenable for single valued comparisons.

In the case of PD, this distance corresponds to the inner nuclear layer where dopaminergic neurons are found. The inner nuclear layer contains dopaminergic neurons. Their loss is a hallmark of PD.

Next in the inventive method can be the three dimensional re-creation of the foveal architecture based color-coded picture of the foveal pit of the subject. This three dimensional re-creation can be displayed on a display device, such as a computer monitor or similar device. The inventive model, discussed in more detail below, receives the thickness values obtained in accordance with the above steps. Accordingly, the obtained thickness values can be entered into the inventive model. Numerical solutions for patient parameters, e.g., each parameter for the PD, and for control parameters, e.g., each parameter for control, are obtained. The percent of change of patient parameters versus control parameters can be determined.

Figure 2:
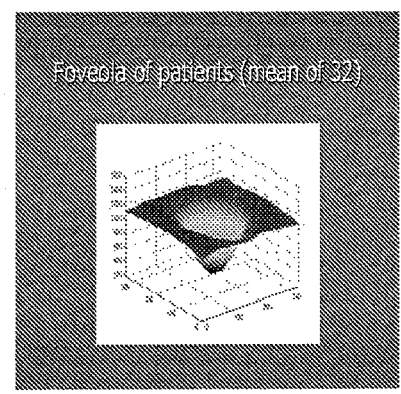
FIG. 2 shows an average or composite foveola of patients or subjects with abnormalities.
Figure 3:
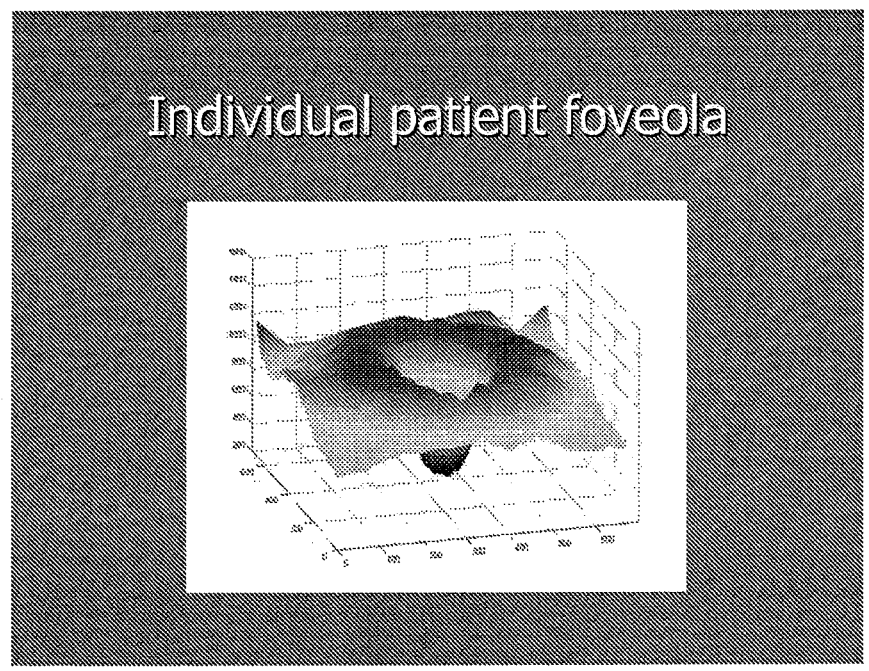
FIG. 3 shows an individual patient foveola.

FIGS. 1-3 show this three dimensional foveal architecture, in which thickness is color-coded and thickness values are in microns. FIG. 1 shows a normal foveola (mean of 20) while FIG. 2 shows an average or composite foveola of patients or subjects with abnormalities (mean of 32). FIG. 3 shows an individual patient foveola. These figures illustrate the difference in the shape of the foveal pit (crater), including the thickness (height) of the crater, for the composite, as shown in FIG. 1, for the abnormal patients, as shown in FIG. 2, and for an individual subject, as shown in FIG. 3.

Figure 4:
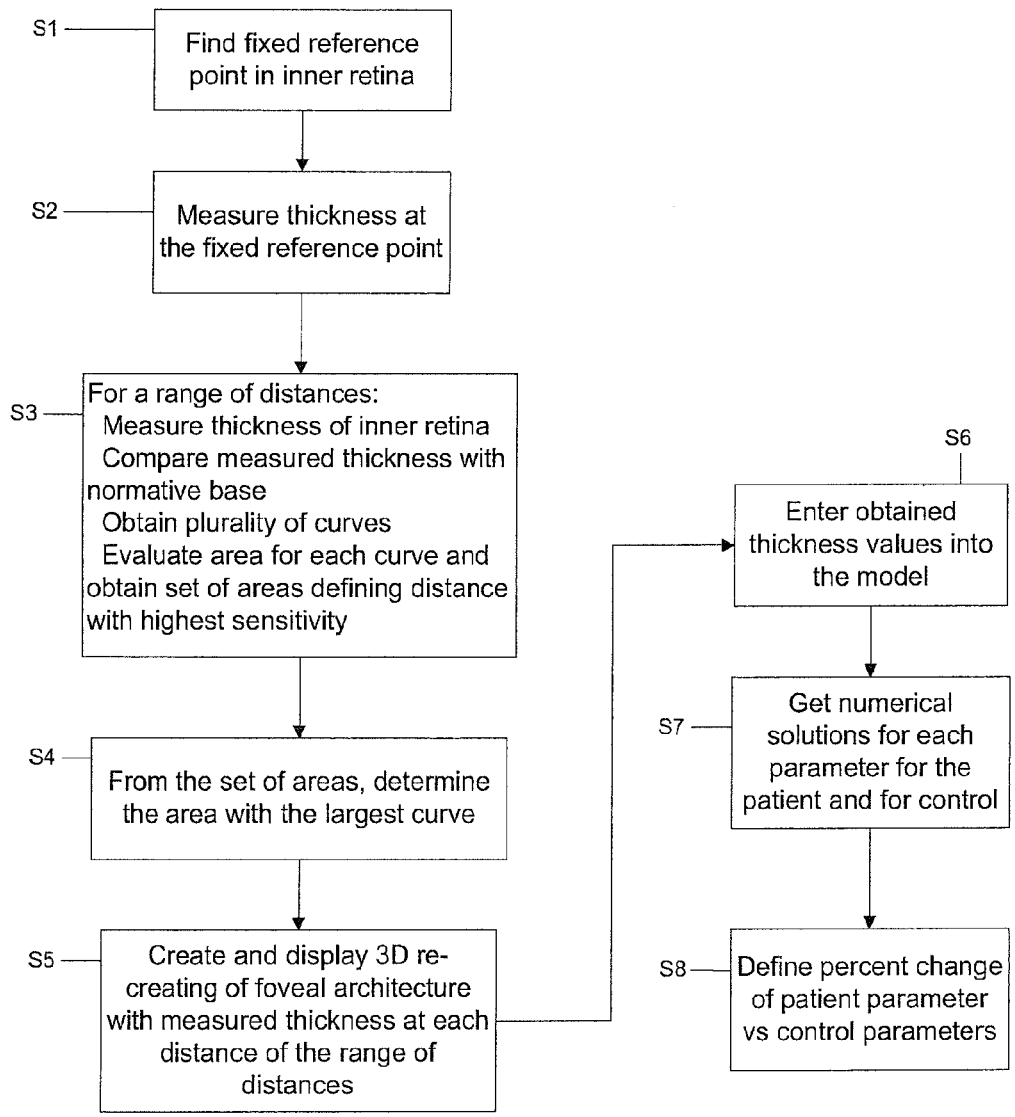
FIG. 4 is a flow diagram of an embodiment of the inventive method.

FIG. 4 shows a flow diagram of an embodiment of the invention. In step S1, find a fixed reference point, e.g., foveola or center of a pit, in the inner retina. In step S2, measure the thickness at this fixed reference point. In step S3, for a range of finely sampled distances, perform the following. Measure the thickness of the inner retina; compare the measured thickness with a normative base such as data developed on healthy subjects for the appropriate age group, the comparison, which can be performed using receiver operator characteristics, obtaining curves for signal/noise ratios. Also for each of the finely sampled distances, evaluate each of the obtained curves and obtain a set of areas defining the distance from the foveola where the highest sensitivity discriminates the subject's retina from healthy controls. In step S4, from the set of curves, determine the curve with the largest area.

Create and display the three dimensional foveal architecture with measured thickness at each finely sampled distance in step S5. In step S6, enter the obtained thickness values into the model. In step S7, get numerical solutions for each parameter of the model, for both PD, e.g., patients, and control. In step S8, define the percent change of the patient parameters versus the control parameters.

In the inventive technology, the data of each recording can be acquired, rather than measuring thickness from images created by the OCT manufacturers' programs. Acquiring the data means obtaining volumes of individual pixels sampled in small steps (0.25 mm for "0" and 0.3 mm for the Zeiss Cirrus ("Z") spectral domain OCT.

All of the manufacturers' programs quantify the Nerve Fiber Layer (NFL) thickness around the optic disc. Given the effect of PD in the preganglionic retina, the source of the NFL, that is, the thickness at the macular area of the PD retina, is examined. Using "0", the thickness of the ganglion cell complex can be originally quantified for the cell bodies of the macular nerve fibers. In one example, twenty-seven patients and twenty-seven control subjects can be quantified for the cell bodies of the macular nerve fibers. On the "0" besides ganglion cells, the Ganglion cell complex (GC) also includes the inner plexiform layer, consisting of processes and interconnections of amacrine cells. Above all, focus is on the fovea because a thinning of the fovealpit in PD had previously been shown. The so-called foveal pit is easily recognizable in the OCT cross sections. As discussed above, what distinguishes the normal foval pit from other retinal areas is that in the center of the foval pit, the inner retinal layers are very thin and on the slope of the foval pit, different retinal layers begin to emerge. Thus quantifying retinal thickness on the slope could permit inferences to be made regarding thickness of different layers with different cellular composition.

Figure 5:
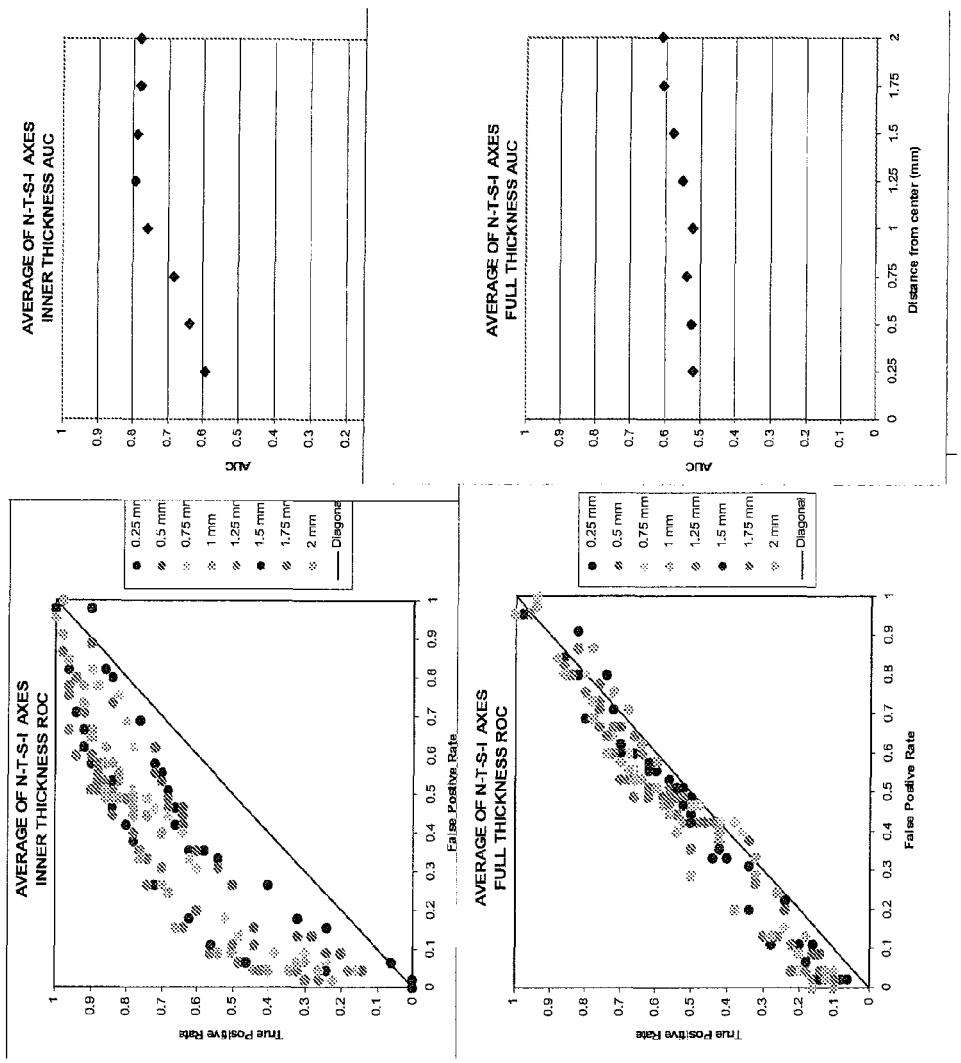
FIG. 5 shows ROC analyses and AUC calculations.

The distance from the foveola at which PD foveae are best discriminated from control retinae can be determined. ROC analyses and their corresponding Area under the Curve (AUC) calculations, illustrated in FIG. 5, can be used to calculate this distance.

Figure 6:
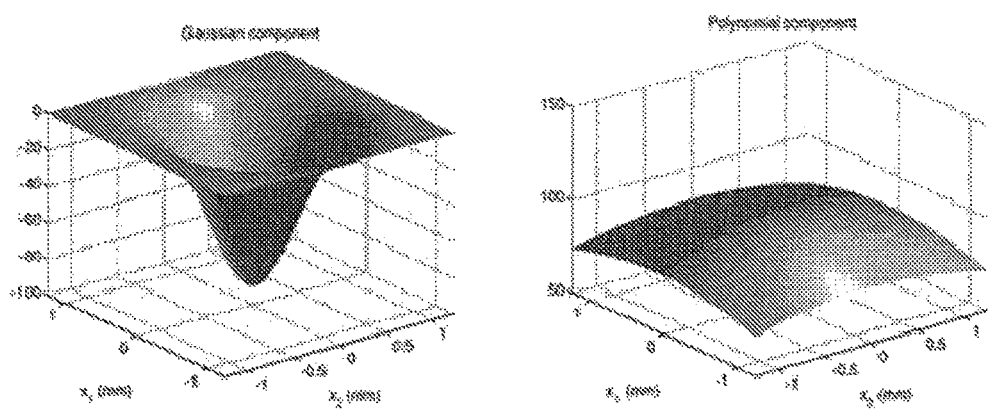
FIG. 6 shows the two components of the inventive model.

As high "true positive rates" and low "false positive rates" represent desired circumstances, curves that integrate most closely to a value of one (1) are considered ideal. The AUC reveals that the inner retinal thickness comparison at radial distances between 0.75 mm and 2.00 mm from the center of the foveola, with a peak at 1.25 mm radially, discriminate optimally between controls and PD patients. FIG. 6 illustrates that the perifoveolar inner retinal zone where the greatest raw thickness difference occurs between control and PD retinae coincides with the results of sensitivity (AUC) calculations. Conversely, FIG. 5 reveals that full retinal thickness measurements have a relatively low sensitivity for discriminating between the two populations, regardless of the directional axis. Full thickness at radial distances beyond 1.75 mm may discriminate between controls and PD patients, but considering both the inner and full retinal measurements, full thickness measurements likely attenuate the ability of OCT to make this discrimination.

In order to quantify the shape change of the fovea in PD, an equation can be used to describe the foveal pit in both healthy controls and in PD. The inventive model associated with the equation is based on actual inner retinal layer thickness data. This is critical for comparing healthy and PD subjects since the results described above show that inner, not FRT (full retinal thickness), distinguishes between PD and controls. In addition, the inventive model differs from a previous mathematical model of the human fovea as the difference of two Gaussians. The equation in the inventive model is smooth and allows rigorous comparison between two instruments.

The model consists of two components: a second-order bivariate polynomial and a zero-mean bivariate Gaussian function. The polynomial component can capture the coarse behavior; the Gaussian component can capture the dip at a finer scale. The model includes a total of seven parameters: four for the polynomial component and three for the Gaussian component. As the equation in PD shows, one parameter of the polynomial (A11 and A12) makes the largest difference (more than fourfold change) between controls and patients.

OCT data of retinal thickness at each radial distance from the foveola (up to 2 mm) are based on the quantification available through the spectral reflectance values at each pixel obtained in a matrix of 18 by 18. These values can be exported into a numerical computing environment, such as the MATLAB environment, and the data can be reconstructed in a shape using the fovea for each individual eye and then for the mean of all eyes. The mean foveal pit in PD and in controls illustrates in three dimensions the difference between control and PD eyes shown in FIG. 1. First, as shown in FIG. 2, the total thickness of the pit extending from to foveola to about 2 mm radial distance is reduced in PD. Second, the slope of the foveal pit is shallower in PD. This is due to quantified tissue loss, which is most evident from 0.75 to 1.5 radial distance. The shape of both the healthy and PD fovea can then be modeled, using the following formula as a parametric model of the foveal pit thickness.

$$f(x_1, x_2) = A_0 + A_{11}x_1 + A_{12}x_1^2 + A_{22}x_2^2 + K\exp\left(-\frac{x_1^2}{2\sigma_1^2} - \frac{x_2^2}{2\sigma_2^2}\right)$$

As discussed above, the model consists of two components: a second-order bivariate polynomial and a zero-mean bivariate Gaussian function. In the polynomial component, the term $x_2$ can be omitted; this term would be present in a general second-order bivariate polynomial because the data is practically symmetric with respect to this dimension. The Gaussian function in the model is not constrained to have unit area because the data is not normalized in this way and because the tails of the Gaussian extend beyond the window of the model.

Initially a difference of two Gaussians models for the foveal pit is evaluated, but the wider of the two Gaussians is not well determined numerically because only the middle portion of the wider Gaussian is covering the central fovea being analyzed, that is, the variance (sigma) of the wider of the two Gaussians is not well determined from the data and the optimization of the parameters is not well conditioned.

In order to obtain the parameters of the model from data, an optimization approach can be used. Specifically, the volume between the model and the data can be minimized. The minimization problem can be written as follows.

$$\underset{p}{\operatorname{argmin}} \int_{x_1} \int_{x_2} |f(x_1, x_2) - d(x_1, x_2)| dx_1 dx_2$$

Where p is the parameter set, p={A0, A11, A12, A21, K, $\sigma_1$, $\sigma_2$}.

In practice, the integral is implemented as a finite summation over the area of interest. Here, $d(x_1, x_2)$ represents the data (PD or control) and $f(x_1, x_2)$ depends on the seven parameters discussed above. Because no closed form solution exists to this minimization problem, a numerical optimization algorithm can be used. In one embodiment, the computation can be performed using Matlab (Version 7.8) with the function fmin search which uses the Nelder-Mead simplex optimization algorithm. The three dimensional representation of the foveal model, both for healthy controls and PD patients, are shown in FIG. 6.

In the inventive model, K represents the full thickness of the foveola (center). Parameters A11 and A12 represent the linear slopes (two dimensions) and parameters A21 and A22 represent the non-linear, e.g., curved, portions of the slopes. Sigmas are the width of the Gaussian cones of the fovea.

In one embodiment, the model control values can be as shown in Table 1.

TABLE 1

| Optovue 1 | Optovue 2 using a second cohort | Cirrus, same cohort as Optovue2 |
|---|---|---|
| A0 = 107.087298 | A0 = 105.339141 | A0 = 129.663819 |
| A11 = 3.814114 | A11 = 3.521559 | A11 = 3.877248 |
| A12 = −9.378914 | A12 = −9.169342 | A12 = −7.062941 |
| A22 = −9.479387 | A22 = −9.434094 | A22 = −4.775364 |
| K = −106.983716 | K = −103.664199 | K = −125.195091 |
| $\sigma'_1$ = 0.449586 | $\sigma'_1$ = 0.458129 | $\sigma'_1$ = 0.468046 |
| $\sigma'$ = 0.365402 | $\sigma'$ = 0.375568 | $\sigma'$ = 0.36576 |

Comparing the model parameters for controls and PD patients shows that the difference was by far most evident in the term A11 which shows an almost four fold change in PD.

For a diagnostic application of OCT, ultimately patients with concurrent ophthalmic or medical conditions should not be excluded but rather a statistical model approach using multivariate analysis will have to be developed. In the search for a quantitative tool to use as a biomarker for PD (i.e. SD-OCT), a larger normative database is needed for the parametric analysis of the effects of age, race, gender and axial length on the inner foveal retina. Neurodegenerative diseases increase with age and a number of them have been shown to affect the retina. Both our patients and controls were selected based on identical and rigorous ophthalmological AND neurological inclusion and exclusion criteria. Our study points to the importance of strict neurological selection criteria in aged subjects presumed to be "controls". Rigorous standards should be used when building a large, "gold standard" normative database of SD-OCT in aged controls.

An exemplary study employing the novel technique follows. The objective of this study is to quantify retinal thickness in patients with Parkinson disease (PD).

In this study, forty-five (45) eyes of twenty-four (24) PD patients and thirty-one (31) eyes of seventeen (17) control subjects underwent a comprehensive ophthalmologic examination. We used optical coherence tomography (OCT) to examine retinal thickness, separately quantifying the inner and outer retinal layers. Intraocular pressure was measured by Goldmann applanation tonometry.

The study participants or subjects were consecutive patients who were diagnosed as having idiopathic PD, based on the accepted UK Brain Bank criteria. These patients were enrolled in the study by neurologists with a special interest in PD. Exclusion criteria were coincident posterior-pole disease, such as macular degeneration or any optic neuropathy due to glaucoma or ischemic optic neuropathy. The erythrocyte sedimentation rate, a potentially relevant laboratory value, was normal in all study participants. The presumptive diagnosis of glaucoma was based on a history of the use of glaucoma medications, increased cupping of the optic nerve, elevated IOP (>21 mm Hg), and/or glaucomatous visual field defects. All study participants had a best-corrected visual acuity of 20/30 or better. Thirteen (13) patients had Humphrey 30-2 visual field tested. The area of the retina evaluated by our OCT corresponds to the central/paracentral area of the visual field. None of the patients showed central/paracentral scotoma on routine visual field testing. Nine (9) patients had their baseline ophthalmologic examination performed by ophthalmologists who provided their routine care, whereas the other patients underwent a comprehensive ophthalmologic examination by one of the co-investigator ophthalmologists involved in this study.

We studied forty-six (46) consecutive eyes of 23 PD patients. All PD patients enrolled were relatively early in their disease course, with an average duration of 2.9 years. The mean (SD) ages of the healthy subjects and PD patients were 63.5 (10.7) years and 64.0 (6.52) years (P=0.77). Twelve (52%) of the PD patients were undergoing pharmacologic therapies that had stabilized their disease, whereas eleven had not yet been treated with dopaminergic agents (de novo patients). Of the treated PD patients, seven were treated with presynaptic (levodopa) medications, four were taking a combination of levodopa and a dopamine receptor agonist, and one was taking pramipexole alone. Their disease stages ranged from two to three, with a mean of 2.5.

We used Fourier-domain OCT, e.g., RTvue; Optovue, Inc; Fremont, Calif., with an imaging speed of approximately 25,000 axial scans per second, which is approximately 50 times faster than time-domain detection found in time-domain OCT. Because a PD OCT protocol does not exist, the standard glaucoma protocol, which includes Nerve Head Map (NHM4) and Macula Map (MM7) scans (Optovue, Inc), was performed for all PD patients. The IRL includes the nerve fiber layer, the ganglion cell layer, and the inner-plexiform layer, whereas the ORL includes the layers starting from the inner nuclear layer up to and including the retinal pigment epithelium. The retinal layer measurements were 6×6-mm sections of the macula. Scans with artifacts such as motion and media were eliminated. Eyes of healthy (control) subjects were examined in the same way.

Statistical analysis was performed using descriptive statistics and analyses of variance. To assess the reproducibility of data obtained with our instrument, we compared two consecutive OCT measurements in seven healthy controls (13 eyes) in one-week intervals. The mean IRL change was 1.25 µm. These data compare favorably with the stability data of the OCT equipment (Optovue), which claim an average variation of only 5 µm. The variability obtained with our equipment is comparable with results obtained with other equipment, such as Heidelberg retinal tomography devices.

Figure 7:
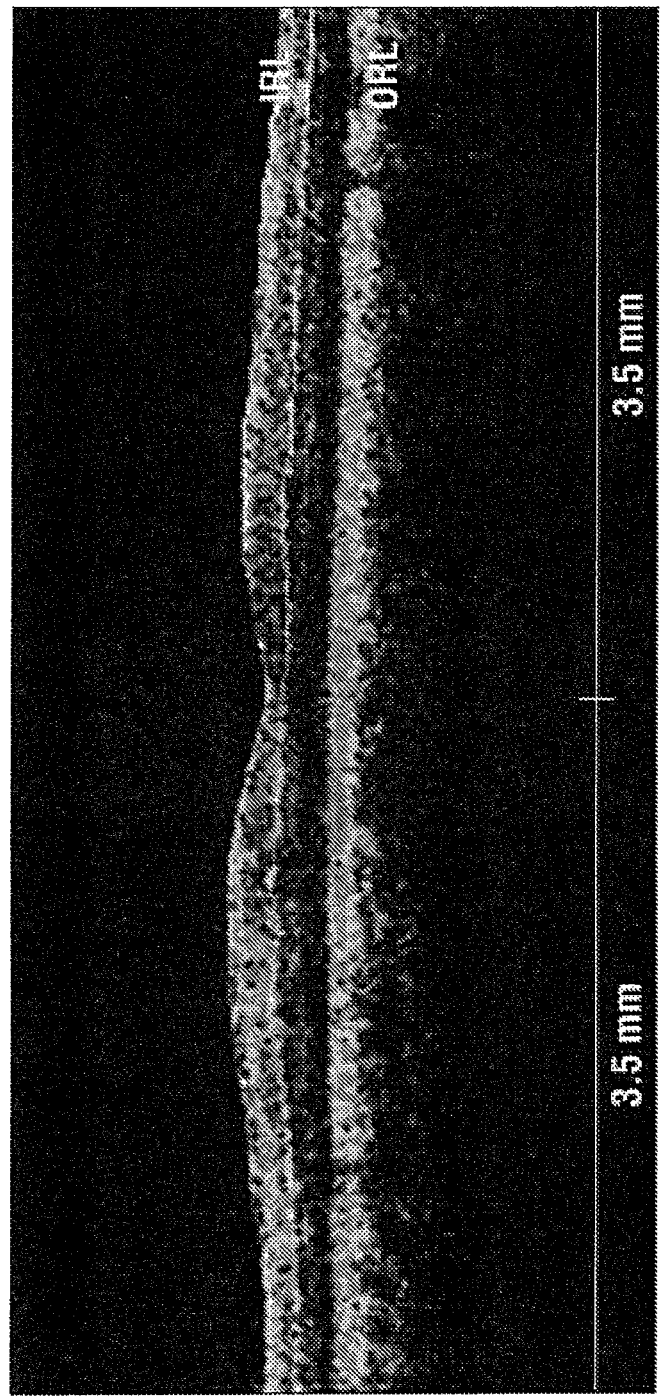
FIG. 7 shows the retina of a healthy individual.
Figure 8:
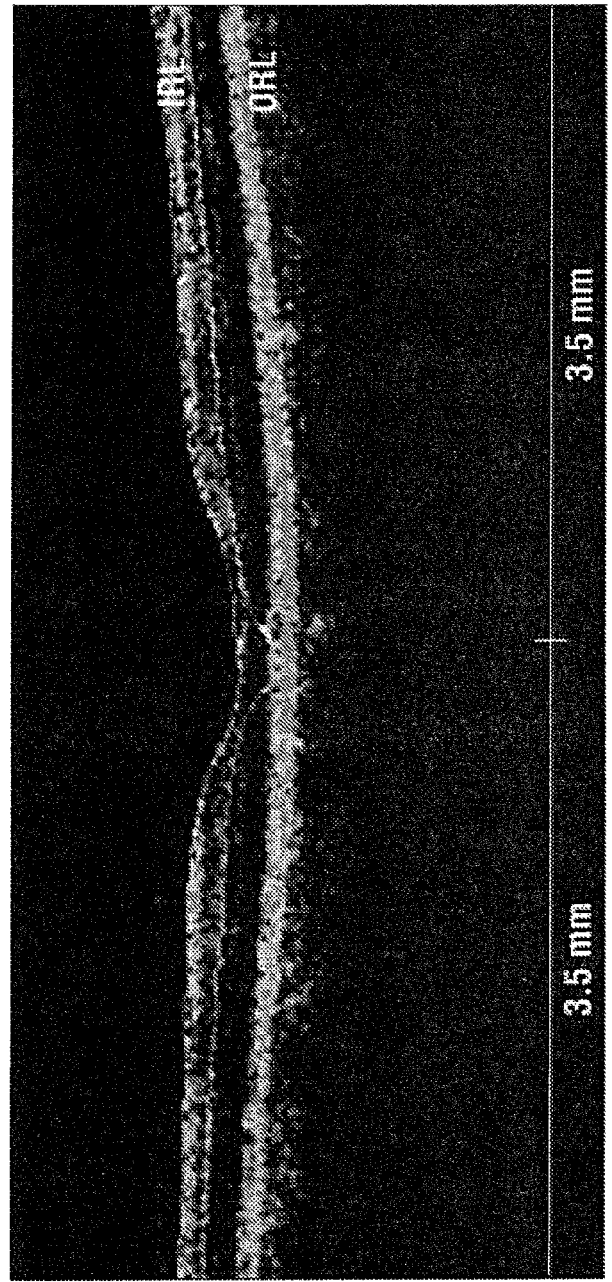
FIG. 8 shows the retina of a patient with Parkinson Disease (PD).

FIG. 7 shows the retina of a healthy individual and FIG. 8 shows a patient with PD; both subjects are roughly the same age. In FIGS. 7 and 8, IRL indicates inner retinal layer and ORL indicates outer retinal layer.

The mean (SD) inferior inner retinal layer ("IRL") thickness of healthy eyes vs PD eyes was 104.0 (23.5) µm vs 89.83 (11.1) µm (P=0.01). The mean superior IRL thickness of healthy eyes vs PD eyes was 103.5 (24.3) µm vs 88.79 (11.3) µm (P=0.01). Clearly, the inferior and superior IRLs are similarly affected in PD patients, and the paramacular inner retina is approximately 15% thinner than the retina of PD patients in age-matched control subjects.

The outer retinal layer ("ORL") thickness was also analyzed in the same manner as the IRL. The mean (SD) superior ORL thickness of healthy eyes vs PD eyes was 170.2 (+/−23.8) µm vs 170.4 (+/−7.67) µm (P=0.88). The mean (SD) inferior ORL thickness of healthy eyes vs PD eyes was 168.2 (+/−22.9) µm vs 167.9 (+/−7.86) µm (P=0.99). A factorial analysis of variance (general linear model) was used to examine if the difference between the right and left eye was dependent on PD diagnosis using the interaction between 2 factors: laterality (right, left eye) and PD diagnosis (PD, no PD). This interaction was not significant for either the superior or inferior IRL or ORL.

FIG. 9 shows a table of retinal thickness of healthy individuals and PD patients. The left-most column of FIG. 9 is retinal area including Superior IRL, Inferior IRL, Superior ORL and Inferior ORL. Retinal thickness is shown for healthy individuals in the second column from the left, and retinal thickness is shown for PD patients in the third column from the left. The P value is shown in the column on the far right. The retinal thickness data is presented in millimeters ("µm"). The table illustrates a significant difference in thickness of the IRL between healthy subjects and PD patients but a lesser difference in thickness of the ORL between healthy subjects and PD patients.

Figure 10:
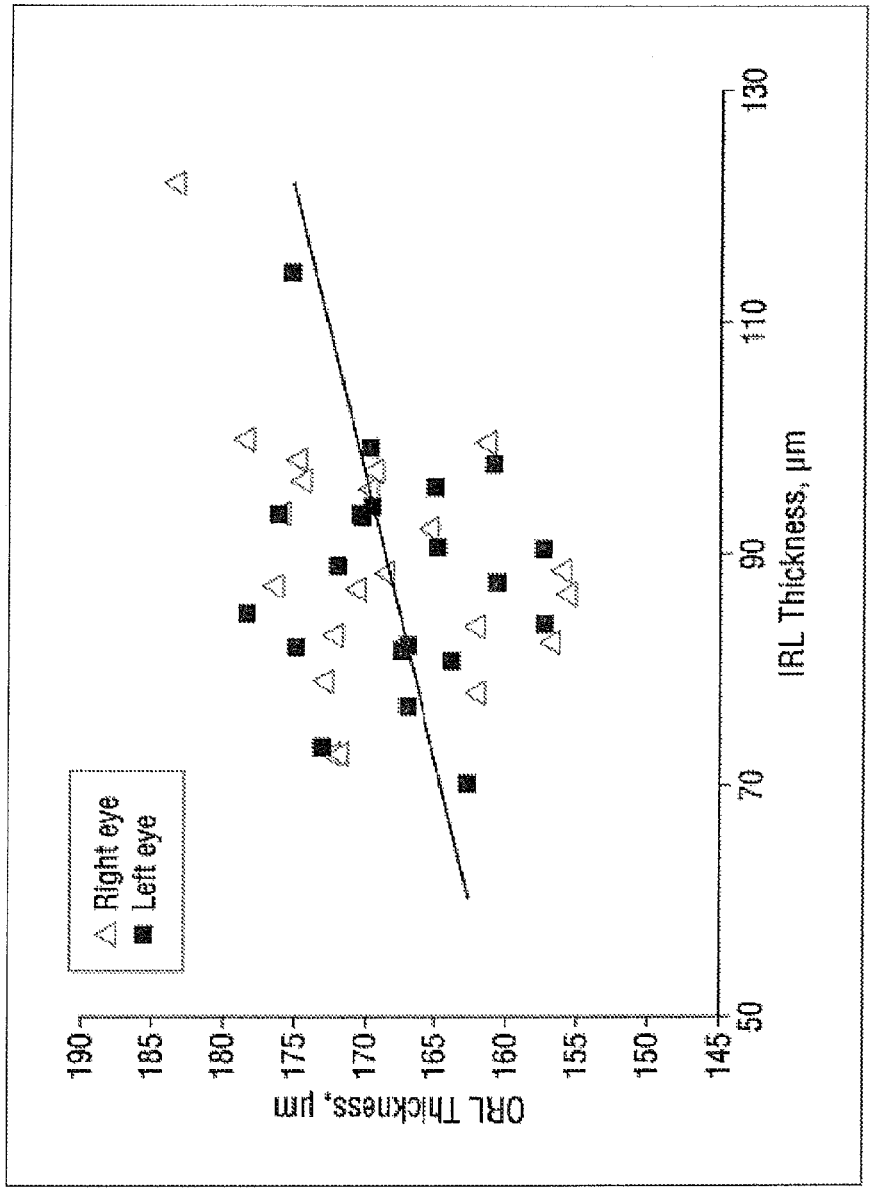
FIG. 10 is a graph illustrating correlation between the outer retinal layer and the inner retinal layer thickness of the left and right eyes of patients with relatively early Parkinson disease.
Figure 11:
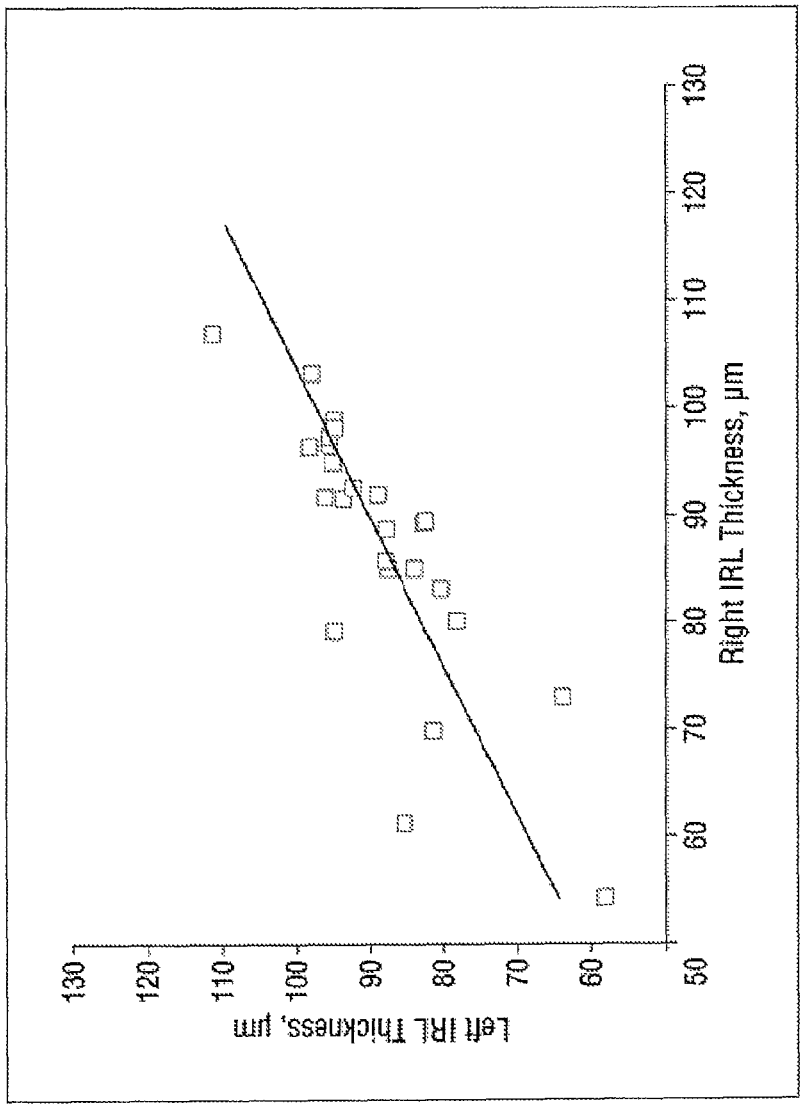
FIG. 11 is a graph illustrating correlation between the inner retinal layer thickness of the left and right eyes of patients with relatively early Parkinson disease.

FIG. 10 illustrates a correlation between the inner retinal layer and the outer retinal layer of thickness of left and right eyes of patients with relatively early PD (r=0.31). The corresponding statistics revealed a correlation coefficient of 0.82. FIG. 11 shows a correlation between the left and right IRL thickness of patients with relatively early PD (r=0.82). The corresponding statistics revealed a correlation coefficient of 0.82. Further, an insignificant correlation was also found between IRL and ORL thickness in the eyes of patients with relatively early PD. The corresponding statistics revealed a correlation coefficient of 0.33.

The effect of treatment was as follows. The mean (SD) superior nerve fiber layer thickness measurements of the treated eyes and untreated eyes were 87.0 (+/−11.17) µm and 91.05 (+/−7.14) µm (P=0.25), respectively. The mean (SD) inferior IRL thickness measurements of the treated eyes and untreated eyes were 89.51 (+/−9.52) µm and 91.04 (+/−8.12) µm (P=0.67), respectively. The mean (SD) superior ORL thickness measurements of the treated eyes and untreated eyes were 171.8 (+/−5.59) µm and 168.7 (+/−9.8 µm) (P=0.20), respectively. The mean (SD) inferior ORL thickness of the treated eyes and untreated eyes was 169.2 (+/−6.02) µm and 164.4 (+/−10.01) µm (P=0.45), respectively.

The time elapsed from PD diagnosis compared with the severity of retinal findings was not statistically significant (P=0.11). The mean (SD) IOP was 13.6 (+/−2.7) mm Hg in PD patients. The correlation of IOP to nerve fiber layer thickness was not statistically significant (r=0.26, P=0.034).

The mean (SD) ages of the patients with PD and healthy subjects were 64.0 (6.5) years vs 63.5 (10.7) years (P=0.77). The mean (SD) intraocular pressure was 13.6 (+/−2.7) mm Hg in the PD patients. No difference was found in either the superior or inferior outer retinal layer thickness of PD vs control eyes. The mean (SD) superior inner retinal layer thickness of PD vs control eyes was 88.79 (11.3) µm vs 103.5 (24.3) µm (P=0.01), and the mean inferior inner retinal layer thickness was 89.83 (11.1) µm vs 104.0 (23.5) µm (P=0.01).

Some conclusions that can be made from this study include the following. The inner retinal layer is significantly thinner in PD patients than in healthy subjects. Idiopathic PD, distinct from glaucoma, needs to be considered in the differential diagnosis of retinal nerve fiber layer thinning. Our study demonstrates a thinning of the IRL in the macular region in PD eyes. Others have reported a stronger effect in the inferior peripapillary quadrant. Our results in PD suggest that the mean thickness of both superior and inferior macular hemispheres is roughly equal. However, looking at individual results, we found that 58% of the superior and 73% of the inferior IRL thickness of PD eyes fell outside one SD. When studying the same patients in 1.5 SDs, 47% of the superior PD IRL and 62% of inferior PD IRL fell outside the range. Clearly, a further comparison of inferior and superior IRL is needed for the paramacular region in a larger number of patients.

Recently, others have reported on the correlation of disease severity with inner foveal but without macular or peripapillary thickness in 17 PD eyes. We examined a 6-mm macular section, which correlates with 17° of central vision. The IRL contains both the ganglion and the amacrine cell layers and is approximately 15% to 20% thinned in this region of the PD retina. Perhaps this modest loss is the reason for the absence of disc pallor in PD despite ganglion cell damage. However, the 15% to 20% loss in total IRL thickness does not necessarily cause a minor loss as far as vision is concerned.

Although visual acuity is only minimally affected in patients with well-corrected PD, they lose foveal CS to patterns to which healthy observers are most sensitive, that is, those that need the least contrast to detect. However, levodopa treatment improves CS.

The PERG is a measure of retinal ganglion cell activity. In both PD and the monkey model, PERG shows a specific spatial frequency deficit similar to the spatial frequency selective CS loss in PD. Spatial frequency is one standard measure of the fineness or coarseness of the visual stimulus; it consists of alternating dark and bright bands (grating pattern). In healthy observers and monkeys, when PERG response or contrast sensitivity is plotted against spatial frequency, the resulting curve is non-monotonic: it shows a peak that represents the best visible spatial frequency pattern. This is called spatial frequency tuning. Tuning reflects the interplay of antagonistic center or surround organization of foveal ganglion cell receptive fields. Tuning is attenuated or absent in CS or PERG in PD patients. On the basis of the effects of selective $D_1$ and $D_2$ receptor blockers on PERG of the monkey, we modeled the preganglionic dopaminergic circuit, which modulates the balance of center and surrounds the organization of foveal ganglion cells of the primate. The model quantifies the way that dopaminergic amacrine cells, although sparsely distributed, control the tuning of foveal ganglion cells via separate $D_1$- and $D_2$-linked receptors and the way that dopaminergic amacrine cell dysfunction may result in absent spatial frequency tuning.

Retinal thinning may be relevant to the early diagnosis and neuroprotective treatment of PD. Most of our patients were in the early stages of the disease. On the basis of the distribution of Lewy bodies at different stages of PD, others have suggested that PD progresses from peripheral to central neurons in a caudocranial direction. It has not been investigated whether Lewy bodies are found in the human retina of PD patients. It needs to be established whether OCT measures contribute a quantitative measure to the early diagnosis of PD other than a constellation of early signs.

The OCT results in PD are potentially relevant for the ophthalmologist. The IRL thinning has been reported in other diseases, such as primary open-angle glaucoma, multiple sclerosis, and Alzheimer disease. The IOP is raised in glaucoma, whereas in our PD patients the IOP was normal. In Alzheimer disease retinal thinning is predominant only in the superior quadrant. Fourier-domain OCT may contribute a quantitative imaging approach to the early diagnosis, treatment, and follow-up of progression of PD.

The novel invention allows the accurate visualization and the diagnosis of the impairment different neurons. The invention is particularly applicable to the diagnosis of neurodegenerative disorders, in particular Parkinson Disease. PD is a prototype neurodegenerative disease. Another one, where some, non-specific OCT data exist is Alzheimer Disease (AD). Similarly to PD, a non-invasive, widely available and relatively inexpensive (less than 100 $) "biomarker" test does not exist. The little available data suggest that OCT, using the novel analytical method disclosed and described herein, may lead to OCTs application not only in PD but other neurodegenerative diseases. However this has not yet been shown. Even if OCT does not have the same diagnostic value in AD as in PD, it will be still useful in the differential diagnosis of PD, given that some of its manifestation overlap with AD.

Various aspects of the present disclosure may be embodied as a program, software, or computer instructions embodied or stored in a computer or machine usable or readable medium, which causes the computer or machine to perform the steps of the method when executed on the computer, processor, CPU, and/or machine. A program storage device readable by a machine, e.g., a computer readable medium, tangibly embodying a program of instructions executable by the machine to perform various functionalities and methods described in the present disclosure is also provided.

The system and method of the present disclosure may be implemented and run on a general-purpose computer or special-purpose computer system. The computer system may be any type of known or will be known systems and may typically include a CPU, processor, memory device, a storage device, input/output devices, internal buses, and/or a communications interface for communicating with other computer systems in conjunction with communication hardware and software, etc.

The computer readable medium could be a computer readable storage medium or a computer readable signal medium. Regarding a computer readable storage medium, it may be, for example, a magnetic, optical, electronic, electromagnetic, infrared, or semiconductor system, apparatus, or device, or any suitable combination of the foregoing; however, the computer readable storage medium is not limited to these examples. Additional particular examples of the computer readable storage medium can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an electrical connection having one or more wires, an optical fiber, an optical storage device, or any appropriate combination of the foregoing; however, the computer readable storage medium is also not limited to these examples. Any tangible medium that can contain, or store a program for use by or in connection with an instruction execution system, apparatus, or device could be a computer readable storage medium.

The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, and/or server. A module may be a component of a device, software, program, or system that implements some "functionality", which can be embodied as software, hardware, firmware, electronic circuitry, or etc.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

What is claimed is:

1. A system for layer-by-layer quantification of the remodeling of the human fovea comprises:
    a display device;
    a model having parameters; and
    a CPU comprising hardware configured to implement a module operable to find a fixed reference point in an inner retina, measure thickness of the inner retina at the fixed reference point, for a range of finely sampled distances starting from the fixed reference point, measure thickness at each finely sampled distance, compare, at each finely sampled distance, the measured thickness with a normative base and obtain a plurality of curves for signal/noise ratios, evaluate area for each curve and obtain a set of areas defining a distance from the fixed reference having highest sensitivity with respect to the fixed reference point compared to the normative base, determine a largest area from the set of areas, create and display, on the display device, a three dimensional re-creation of foveal architecture-based color-coded picture in accordance with the measured thickness at each finely sampled distance and the largest area, enter the measured thickness into the model, obtain numerical solutions for each parameter for a patient and for a control of the model and define percent change of the parameters for the patient versus the parameters for the control.

2. The system according to claim 1, wherein the model comprises a Gaussian function having three parameters and a polynomial function having four parameters.

3. The system according to claim 2, wherein the Gaussian function is a zero-mean bivariate Gaussian function and the polynomial function is a second-order bivariate polynomial.

4. A method for layer-by-layer quantification of the remodeling of the human fovea, comprises steps of:
- finding a fixed reference point in an inner retina;
- measuring the thickness of the inner retina at the fixed reference point;
- for a range of finely sampled distances starting from the fixed reference point,
  - measuring the thickness at each finely sampled distance;
  - comparing, at each finely sampled distance, the measured thickness with a normative base and obtaining a plurality of curves for signal/noise ratios;
  - evaluating area for each curve and obtaining a set of areas defining a distance from the fixed reference having highest sensitivity with respect to the retina compared to the normative base;
  - determining a largest area from the set of areas;
- creating and displaying a three dimensional re-creation of foveal architecture-based color-coded picture in accordance with the measured thickness at each finely sampled distance and the largest area;
- entering the measured thickness into a model having parameters;
- obtaining numerical solutions for each parameter for a patient and for a control of the model; and
- defining percent change of the parameters for the patient versus the parameters for the control.

5. The method according to claim 4, wherein the model comprises a Gaussian function having three parameters and a polynomial function having four parameters.

6. The method according to claim 5, wherein the Gaussian function is a zero-mean bivariate Gaussian function and the polynomial function is a second-order bivariate polynomial.

7. A non-transitory computer readable storage medium storing a program of instructions executable by a machine to perform a method for layer-by-layer quantification of the remodeling of the human fovea, comprising:
- finding a fixed reference point in an inner retina;
- measuring the thickness of the inner retina at the fixed reference point;
- for a range of finely sampled distances starting from the fixed reference point,
  - measuring the thickness at each finely sampled distance;
  - comparing, at each finely sampled distance, the measured thickness with a normative base and obtaining a plurality of curves for signal/noise ratios;
  - evaluating area for each curve and obtaining a set of areas defining a distance from the fixed reference having highest sensitivity with respect to the retina compared to the normative base;
  - determining a largest area from the set of areas;
- creating and displaying a three dimensional re-creation of foveal architecture-based color-coded picture in accordance with the measured thickness at each finely sampled distance and the largest area;
- entering the measured thickness into a model having parameters;
- obtaining numerical solutions for each parameter for a patient and for a control of the model; and
- defining percent change of the parameters for the patient versus the parameters for the control.

8. The program according to claim 7, wherein the model comprises a Gaussian function having three parameters and a polynomial function having four parameters.

9. The program according to claim 8, wherein the Gaussian function is a zero-mean bivariate Gaussian function and the polynomial function is a second-order bivariate polynomial.

* * * * *